United States Patent
Kamtekar et al.

(10) Patent No.: US 11,349,086 B2
(45) Date of Patent: May 31, 2022

(54) COMPOUND, COMPOSITION AND ORGANIC LIGHT-EMITTING DEVICE

(71) Applicants: Cambridge Display Technology Limited, Godmanchester (GB); Sumitomo Chemical Company Limited, Tokyo (JP)

(72) Inventors: Kiran Kamtekar, Godmanchester (GB); William Tarran, Godmanchester (GB); Martin Humphries, Godmanchester (GB); Florence Bourcet, Godmanchester (GB)

(73) Assignees: Cambridge Display Technology Limited, Godmanchester (GB); Sumitomo Chemical Company Limited, Tokyo (JP)

(*) Notice: Subject to any disclaimer, the term of this patent is extended or adjusted under 35 U.S.C. 154(b) by 654 days.

(21) Appl. No.: 16/078,914

(22) PCT Filed: Feb. 20, 2017

(86) PCT No.: PCT/GB2017/050434
§ 371 (c)(1),
(2) Date: Aug. 22, 2018

(87) PCT Pub. No.: WO2017/144863
PCT Pub. Date: Aug. 31, 2017

(65) Prior Publication Data
US 2019/0058134 A1    Feb. 21, 2019

(30) Foreign Application Priority Data
Feb. 22, 2016 (GB) .................. 1603039

(51) Int. Cl.
*H01L 51/50* (2006.01)
*H01L 51/00* (2006.01)
(Continued)

(52) U.S. Cl.
CPC ........ *H01L 51/0074* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

| | | |
|---|---|---|
| 2011/0037027 A1 | 2/2011 | Stoessel |
| 2015/0179940 A1 | 6/2015 | Mujica-Fernaud |

(Continued)

FOREIGN PATENT DOCUMENTS

| | | | |
|---|---|---|---|
| EP | 2 428 512 A2 | 3/2012 | |
| JP | 2011-082238 | * 4/2011 | ............ C09K 11/06 |

(Continued)

OTHER PUBLICATIONS

PCT/GB2017/050434, Jun. 21, 2017, International Search Report and Written Opinion.
(Continued)

*Primary Examiner* — Gregory D Clark
(74) *Attorney, Agent, or Firm* — Wolf, Greenfield & Sacks, P.C.

(57) ABSTRACT

A compound of formula (I) or (III) (Formulae (I), (III)) wherein: one Y is a substituent $R^1$ bound directly to the fluorene unit of formula (I) by an $sp^3$-hybridised carbon atom; the other Y is an aryl or heteroaryl group $Ar^1$ that may be unsubstituted or substituted with one or more substituents; $Ar^2$ is an arylene or heteroarylene group; $R^2$ is a substituent; b is 0, 1, 2, 3 or 4; c is 0, 1, 2 or 3; and X is a group of formula (II): (Formula (II)) wherein Z is O or S; $R^3$ independently in each occurrence is a substituent; each x is independently 0, 1, 2 or 3; and * is a bond to the fluorene unit (Continued)

of formula (I). The compounds may be used as host materials for phosphorescent dopants in organic light-emitting devices.

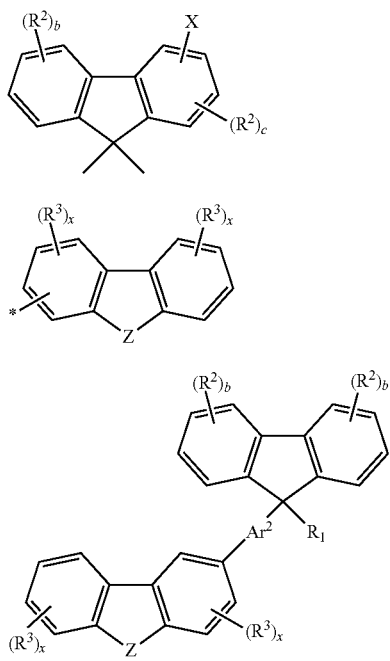

18 Claims, 1 Drawing Sheet

(51) Int. Cl.
C07D 333/76 (2006.01)
C07D 307/91 (2006.01)
C09K 11/06 (2006.01)
H05B 33/14 (2006.01)
C09K 11/02 (2006.01)

(52) U.S. Cl.
CPC ............ *C09K 11/02* (2013.01); *C09K 11/06* (2013.01); *H01L 51/0052* (2013.01); *H01L 51/0073* (2013.01); *H01L 51/0085* (2013.01); *H01L 51/50* (2013.01); *H01L 51/5004* (2013.01); *H01L 51/5016* (2013.01); *H05B 33/14* (2013.01); *H01L 51/5056* (2013.01)

(56) References Cited

U.S. PATENT DOCUMENTS

2015/0179953 A1 6/2015 Mujica-Fernaud
2015/0207075 A1 7/2015 Mujica-Fernaud
2017/0194569 A1* 7/2017 Kim .................... H01L 51/0071

FOREIGN PATENT DOCUMENTS

| JP | 2011-082238 | A | 4/2011 | |
| KR | 10-2014-0099082 | A | 8/2014 | |
| KR | 2014099082 | * | 9/2014 | ............ C09K 11/06 |
| KR | 20150074603 | A | 7/2015 | |
| WO | WO 2014/015937 | A1 | 1/2014 | |
| WO | WO 2014-042420 | A1 | 3/2014 | |
| WO | WO 2015/082056 | A1 | 6/2015 | |
| WO | WO 2015/169412 | A1 | 11/2015 | |

OTHER PUBLICATIONS

GB1603039.7, Dec. 15, 2016, Combined Search and Examination Report.
International Search Report and Written Opinion for International Application No. PCT/GB2017/050434, dated Jun. 21, 2017.
Combined Search and Examination Report for British Application No. GB1603039.7, dated Dec. 15, 2016.
EP 17707106.5, Dec. 3, 2020, European Communication.
European communication dated Dec. 3, 2020 in connection with European Application No. 17707106.5.

* cited by examiner

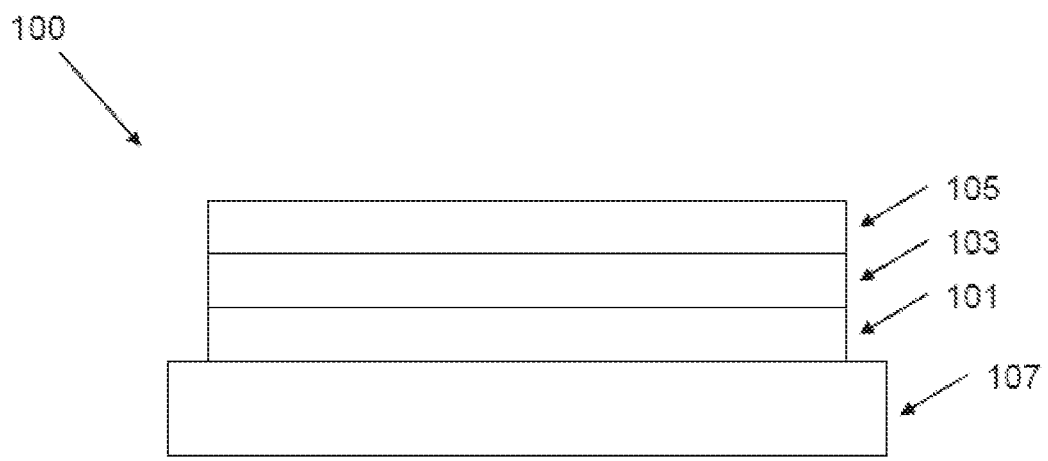

COMPOUND, COMPOSITION AND ORGANIC LIGHT-EMITTING DEVICE

RELATED APPLICATIONS

This Application is a national stage filing under 35 U.S.C. § 371 of international PCT application PCT/GB2017/050434, filed Feb. 20, 2017, which claims priority to United Kingdom patent application GB 1603039.7, filed Feb. 22, 2016, each of which is incorporated herein by reference in its entirety.

FIELD OF THE INVENTION

The invention relates to compounds suitable for use as host materials for light-emitting dopants, in particular phosphorescent dopants, and organic light-emitting devices containing said materials.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Light-emitting materials include small molecule, polymeric and dendrimeric materials. Light-emitting polymers include poly(arylene vinylenes) such as poly(p-phenylene vinylenes) and polymers containing arylene repeat units, such as fluorene repeat units.

A light emitting layer may comprise a host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

Sook et al, J. Mater. Chem., 2011, 21, 14604 discloses host materials DBT1, DBT2 and DBT3:

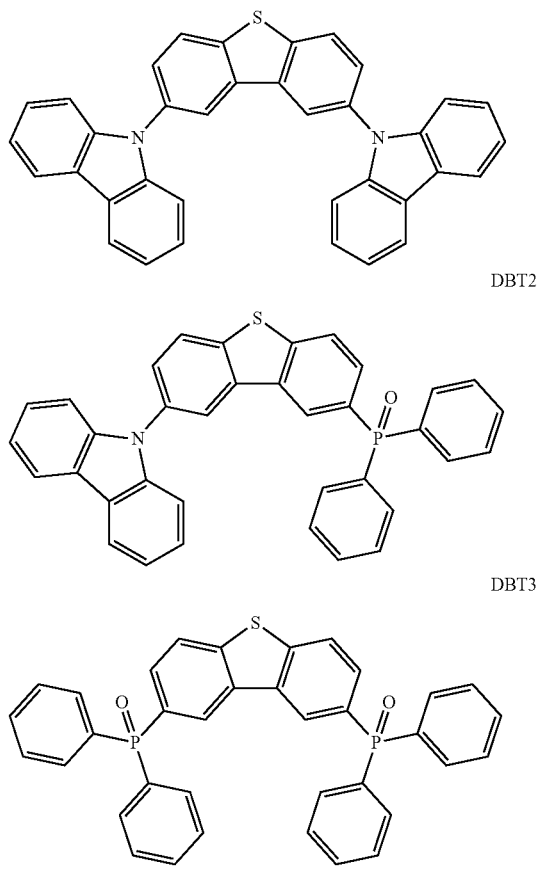

EP 2428512 discloses compounds of formula (G1) in which a1 and a2 separately represent an arylene group:

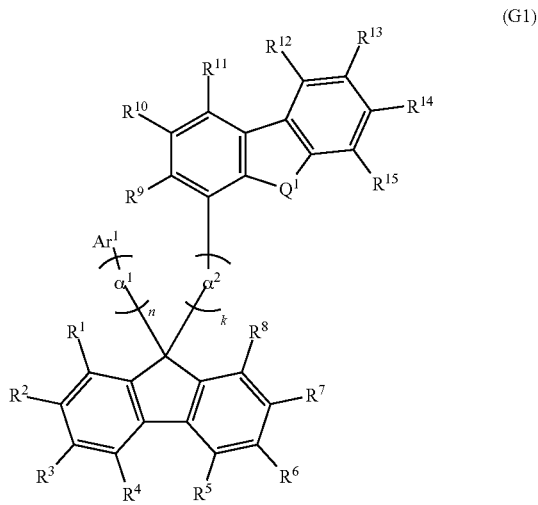

JP 2011/082238 discloses compounds of formula (1) in which at least one of Y1 and Y2 a group of formula (A) and Ar is a group of formula (B).

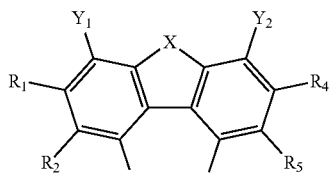

(A)

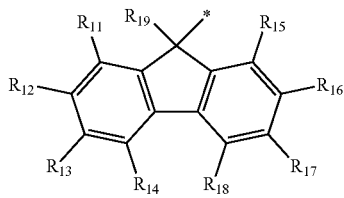

(B)

KR 2014/0099082 discloses compounds having the following formula:

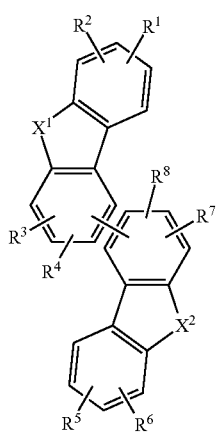

It is an object of the invention to provide host materials for high efficiency organic light-emitting devices.

It is a further object of the invention to provide host materials for blue phosphorescent materials.

It is a further object of the invention to provide solution-processable host materials.

SUMMARY OF THE INVENTION

In a first aspect the invention provides a compound of formula (I)

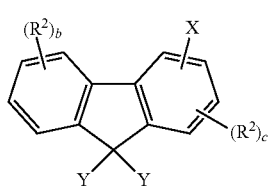

wherein:
one Y is a substituent $R^1$ bound directly to the fluorene unit of formula (I) by an $sp^3$-hybridised carbon atom;

the other Y is an aryl or heteroaryl group $Ar^1$ that may be unsubstituted or substituted with one or more substituents;
$R^2$ is a substituent;
b is 0, 1, 2, 3 or 4;
c is 0, 1, 2 or 3; and
X is a group of formula (II):

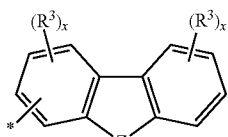

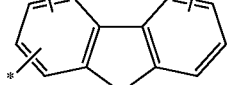

wherein Z is O or S; $R^3$ independently in each occurrence is a substituent; each x is independently 0, 1, 2 or 3; and * is a bond to the fluorene unit of formula (I).

In a second aspect the invention provides a compound of formula (III):

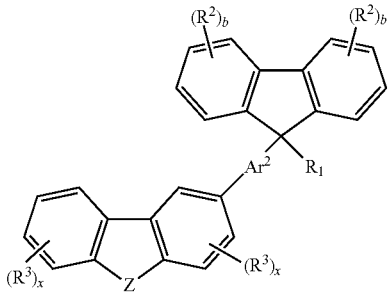

wherein:
$R^1$ is a substituent bound directly to the fluorene unit of formula (I) by an $sp^3$-hybridised carbon atom;
$Ar^2$ is an arylene or heteroarylene group that may be unsubstituted or substituted with one or more substituents;
$R^2$ independently in each occurrence is a substituent;
b is 0, 1, 2, 3 or 4;
Z is O or S;
$R^3$ independently in each occurrence is a substituent; and
each x is independently 0, 1, 2 or 3.

In a third aspect the invention provides a composition comprising a compound according to the first or second aspect and at least one light-emitting dopant.

In a fourth aspect the invention provides a formulation comprising a compound according to the first or second aspect or a composition according to the third aspect and one or more solvents.

In a fifth aspect the invention provides n organic light-emitting device comprising an anode, a cathode and a light-emitting layer between the anode and the cathode wherein the light-emitting layer comprises a compound according to the first or second aspect.

In a sixth aspect the invention provides a method of forming an organic light-emitting device according to the fifth aspect, the method comprising the step of forming the light-emitting layer over one of the anode and the cathode and forming the other of the anode and the cathode over the light-emitting layer.

"Aryl" and "heteroaryl" as used herein includes monocyclic and fused aryl and heteroaryl groups.

DESCRIPTION OF THE DRAWINGS

The invention will now be described in more detail with reference to the drawings in which:

FIG. 1 illustrates an OLED according to an embodiment of the invention.

DETAILED DESCRIPTION OF THE INVENTION

FIG. 1 illustrates an OLED 100 according to an embodiment of the invention comprising an anode 101, a cathode 105 and a light-emitting layer 103 between the anode and cathode. The device 100 is supported on a substrate 107, for example a glass or plastic substrate.

One or more further layers may be provided between the anode 101 and cathode 105, for example hole-transporting layers, electron transporting layers, hole blocking layers and electron blocking layers. The device may contain more than one light-emitting layer.

Preferred device structures include:
Anode/Hole-injection layer/Light-emitting layer/Cathode
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

Preferably, at least one of a hole-transporting layer and hole injection layer is present. Preferably, both a hole injection layer and hole-transporting layer are present.

Light-emitting materials include red, green and blue light-emitting materials.

A blue emitting material may have a photoluminescent spectrum with a peak in the range of 400-490 nm, optionally 420-490 nm.

A green emitting material may have a photoluminescent spectrum with a peak in the range of more than 490 nm up to 580 nm, optionally more than 490 nm up to 540 nm.

A red emitting material may optionally have a peak in its photoluminescent spectrum of more than 580 nm up to 630 nm, optionally 585-625 nm.

The photoluminescence spectrum of a compound of formula (I) may be measured by casting 5 wt % of the material in a polystyrene film onto a quartz substrate and measuring in a nitrogen environment using apparatus C9920-02 supplied by Hamamatsu.

Light-emitting layer 103 contains a compound of formula (I) or (III) doped with one or more luminescent dopants. The light-emitting layer 103 may consist essentially of these materials or may contain one or more further materials, for example one or more charge-transporting materials or one or more further light-emitting materials. When used as a host material for one or more light-emitting dopants, the lowest excited stated singlet ($S^1$) or the lowest excited state triplet ($T_1$) energy level of the compound of formula (I) or (III) is preferably no more than 0.1 eV below that of the light-emitting material, and is more preferably about the same as or higher than that of the light-emitting material in order to avoid quenching of luminescence from the light-emitting dopant.

In the case where the luminescent dopant is a phosphorescent dopant, the compound of formula (I) or (III) preferably has a $T_1$ of greater than 2.8 eV, preferably greater than 3.0 eV.

Triplet energy levels of compounds of formula (I) or (III) and phosphorescent materials may be measured from the energy onset of the phosphorescence spectrum measured by low temperature phosphorescence spectroscopy (Y. V. Romaovskii et al, Physical Review Letters, 2000, 85 (5), p 1027, A. van Dijken et al, Journal of the American Chemical Society, 2004, 126, p 7718).

The compounds of formula (I) and (III) preferably have a HOMO level of at least 5.8 eV from vacuum level, preferably at least 5.9 eV from vacuum level. HOMO and LUMO levels as given herein are as measured by square wave voltammetry.

Preferably, a light-emitting material used with a host compound of formula (I) or (III) has a HOMO level at least 0.1 eV closer to vacuum than the compound of formula (I) or (III), optionally at least 0.5 eV closer to vacuum.

In a preferred embodiment, light-emitting layer 103 contains a compound of formula (I) or (III) and at least one of green and blue phosphorescent light-emitting materials.

Compounds of Formula (I)

$Ar^1$ is optionally selected from $C_{6-20}$ arylenes and 5-20 membered heteroarylenes.

$Ar^1$ may be unsubstituted or substituted with one or more groups $R^4$ wherein $R^4$ in each occurrence is independently a substituent. If present, substituents $R^4$ are optionally selected from branched, linear or cyclic $C_{1-20}$ alkyl wherein one or more non-adjacent C atoms may be replaced with O, S, CO or COO.

$Ar^1$ is preferably phenyl that may be unsubstituted or substituted with one or more substituents $R^4$.

$R^1$ is bound to the 9-position of the fluorene unit of formula (I) through an $sp^a$ hybridised carbon atom. Preferably, $R^1$ is a linear, branched or cyclic $C_{1-20}$ alkyl group, more preferably methyl The compound of formula (I) may have formula (Ia) or (Ib):

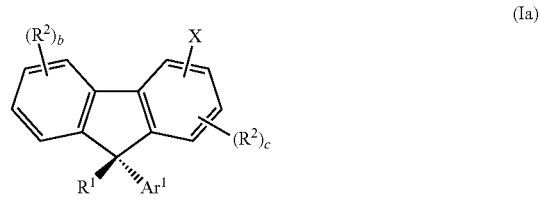

(Ia)

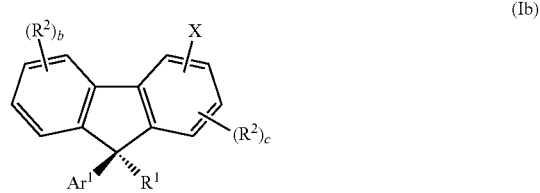

(Ib)

Optionally, the group of formula (II) is selected from formulae (IIa) or (IIb):

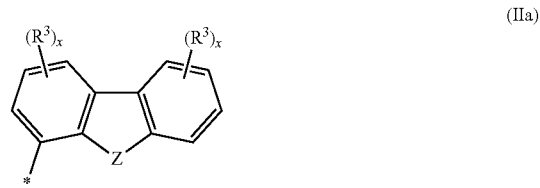

(IIa)

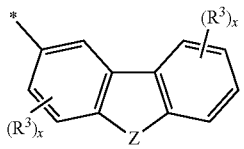

(IIb)

wherein * represents an attachment point of the unit of formula (IIa) or (IIb) to the fluorene unit of formula (I).

If present, $R^2$ and $R^3$ are preferably in each occurrence independently selected from linear, branched or cyclic $C_{1-12}$ alkyl and aryl or heteroaryl, preferably $C_{6-20}$ aryl or 5-20 membered heteroaryl, which may be unsubstituted or substituted with one or more substituents, optionally one or more $C_{1-12}$ alkyl groups.

An aryl or heteroaryl group $R^2$ is preferably substituted at one or both ring atoms adjacent to the ring atom of the aryl or heteroaryl group bound to the fluorene group of formula (III) in order to limit the extent of conjugation in the compound of formula (III).

An aryl or heteroaryl group $R^3$ is preferably substituted at one or both ring atoms adjacent to the ring atom of the aryl or heteroaryl group bound to the dibenzofuran or dibenzothiophene group of formula (III) in order to limit the extent of conjugation in the compound of formula (III).

Preferably, an aryl or heteroaryl group $R^2$ or $R^3$ is phenyl that may be unsubstituted or substituted with one or more substituents.

Preferably, b is 0.

Preferably, c is 0.

Preferably, each x is 0.

Exemplary compounds of formula (I) are:

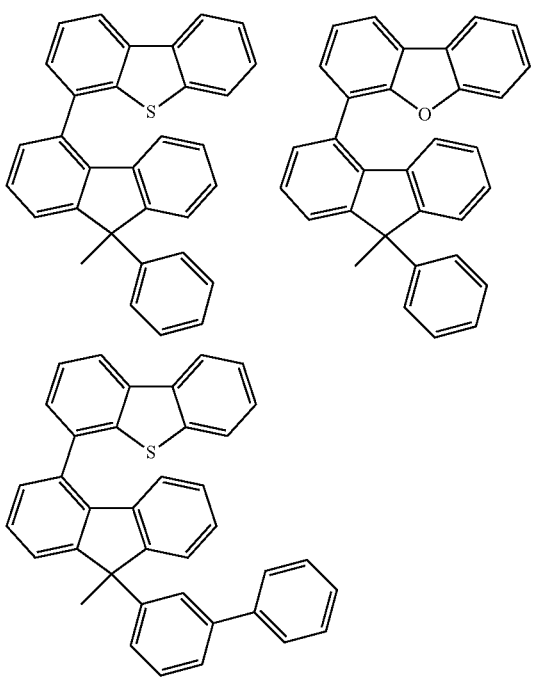

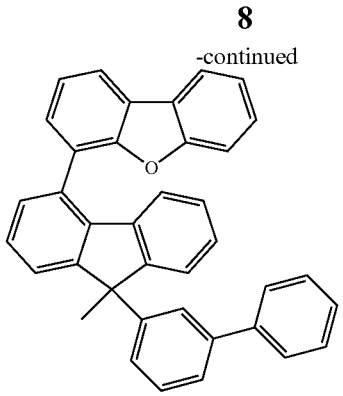

Compounds of Formula (III)

$Ar^2$ is optionally selected from $C_{6-20}$ arylenes and 5-20 membered heteroarylenes. $Ar^2$ may be unsubstituted or substituted with one or more groups $R^4$ wherein $R^4$ in each occurrence is independently a substituent. If present, substituents $R^4$ are optionally selected from branched, linear or cyclic $C_{1-20}$ alkyl wherein one or more non-adjacent C atoms may be replaced with O, S, CO or COO.

$Ar^2$ is preferably phenylene that may be unsubstituted or substituted with one or more substituents $R^4$.

$R^1$ is preferably a $C_{1-20}$ alkyl group.

Optionally, the compound of formula (III) has formula (IIIa):

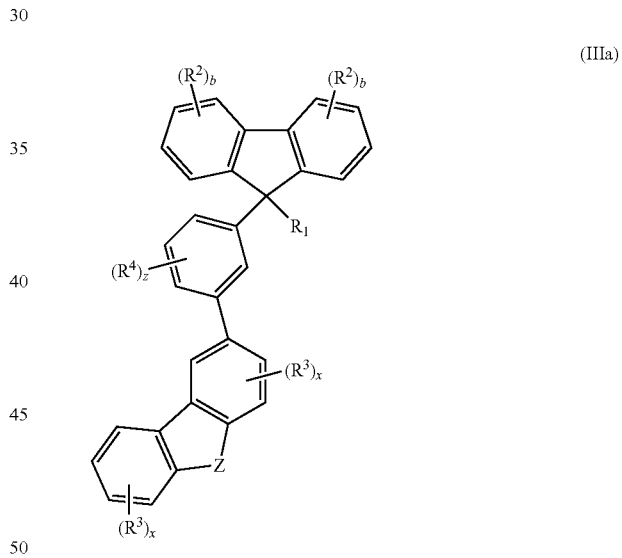

If present, $R^2$ and $R^3$ are preferably in each occurrence independently selected from linear, branched or cyclic $C_{1-12}$ alkyl and aryl or heteroaryl, preferably $C_{6-20}$ aryl or 5-20 membered heteroaryl, which may be unsubstituted or substituted with one or more substituents, optionally one or more $C_{1-12}$ alkyl groups.

An aryl or heteroaryl group $R^2$ is preferably substituted at one or both ring atoms adjacent to the ring atom of the aryl or heteroaryl group bound to the fluorene group of formula (III) in order to limit the extent of conjugation in the compound of formula (III).

An aryl or heteroaryl group $R^3$ is preferably substituted at one or both ring atoms adjacent to the ring atom of the aryl or heteroaryl group bound to the dibenzofuran or dibenzothiophene group of formula (III) in order to limit the extent of conjugation in the compound of formula (III).

Preferably, an aryl or heteroaryl group $R^2$ or $R^3$ is phenyl that may be unsubstituted or substituted with one or more substituents.

b is preferably 0.

x is preferably 0.

z is preferably 0.

Exemplary compounds of formula (III) are:

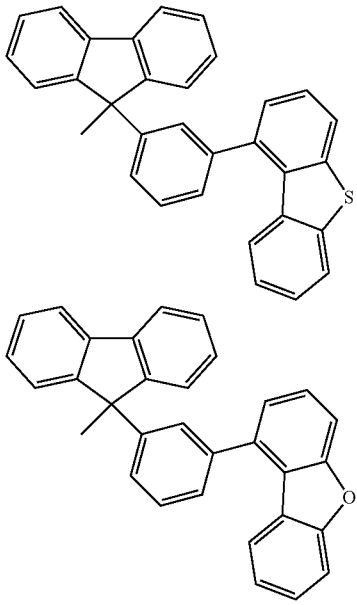

Light-Emitting Compounds

A preferred use of compounds of formulae (I) and (III) is as the host material for a light-emitting material in a light-emitting layer of an OLED.

Suitable light-emitting materials for a light-emitting layer include polymeric, small molecule and dendritic light-emitting materials, each of which may be fluorescent or phosphorescent.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain more than one light-emitting material, for example a mixture of light-emitting materials that together provide white light emission.

A white-emitting OLED may contain a single, white-emitting layer containing a light-emitting composition as described herein, or may contain two or more layers that emit different colours which, in combination, produce white light and wherein at least one of the light emitting layers comprises a composition as described herein.

The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K.

Exemplary phosphorescent compounds have formula (IX):

$$ML^1_q L^2_r L^3_s \qquad (IX)$$

wherein M is a metal; each of $L^1$, $L^2$ and $L^3$ is a coordinating group that independently may be unsubstituted or substituted with one or more substituents; q is a positive integer; r and s are each independently 0 or a positive integer; and the sum of (a·q)+(b·r)+(c·s) is equal to the number of coordination sites available on M, wherein a is the number of coordination sites on $L^1$, b is the number of coordination sites on $L^2$ and c is the number of coordination sites on $L^3$.

a, b and c are preferably each independently 1, 2 or 3. Preferably, $L^1$, $L^2$ and $L^3$ are each a bidentate ligand (a, b and c are each 2). In an embodiment, q is 3 and r and s are 0. In another embodiment, q is 1 or 2; r is 1; and s is 0 or 1, preferably 0.

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (X):

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

Each of $Ar^5$ and $Ar^6$ may carry one or more substituents. Two or more of these substituents may be linked to form a ring, for example an aromatic ring. Preferred substituents are selected from D, F, $C_{1-20}$ alkyl groups wherein one or more non-adjacent C atoms may be replaced with O, S, CO or COO and one or more H atoms may be replaced with F; phenyl or biphenyl that may be unsubstituted or substituted with one or more substituents, optionally one or more $C_1$-10 alkyl or $C_{1-12}$ alkoxy groups; and dendrons.

To achieve red emission, $Ar^5$ may be selected from phenyl, fluorene, naphthyl and $Ar^6$ are selected from quinoline, isoquinoline, thiophene and benzothiophene.

To achieve green emission, $Ar^5$ may be selected from phenyl or fluorene and $Ar^6$ may be pyridine.

To achieve blue emission, $Ar^5$ may be selected from phenyl and $Ar^6$ may be selected from imidazole, pyrazole, triazole and tetrazole.

Examples of bidentate ligands of formula (X) wherein $X^1$ is carbon and $Y^1$ is nitrogen are:

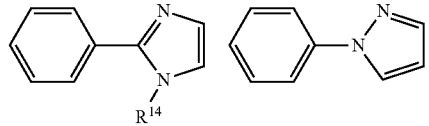

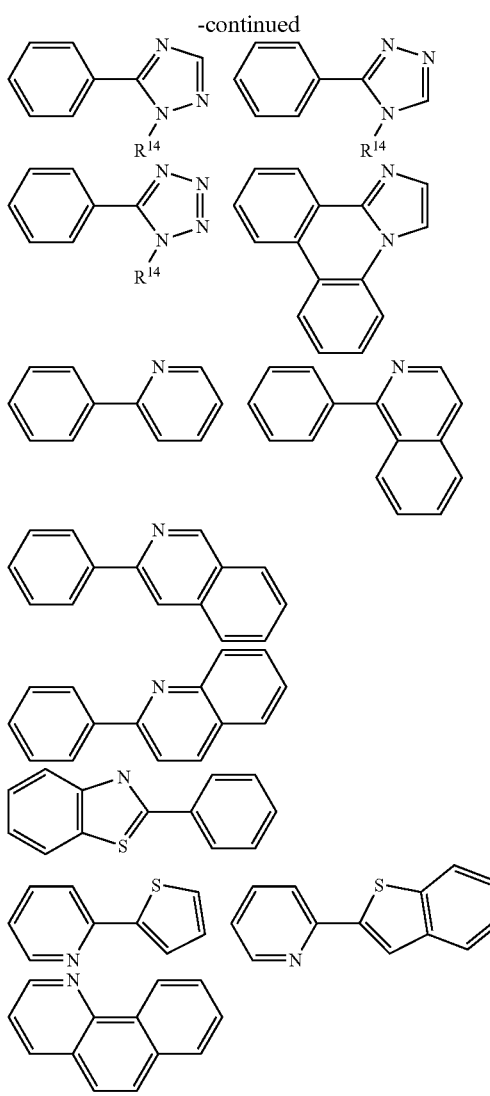

wherein R[14] is a substituent and wherein each C atom may independently be unsubstituted or substituted with a substituent R[15].

Substituents R[14] and R[15] are preferably selected from $C_{1-40}$ hydrocarbyl groups, preferably linear, branched or cyclic $C_{1-20}$ alkyl groups; phenyl or biphenyl which may be unsubstituted or substituted with one or more $C_{1-12}$ alkyl groups; and dendrons.

Other ligands suitable for use with d-block elements include O,O-bidentate ligands, optionally diketonates, O,N-bidentate ligands and N,N bidentate ligands, in particular acetylacetonate (acac), tetrakis-(pyrazol-1-yl)borate, 2-carboxypyridyl, triarylphosphines and pyridine, each of which may be substituted.

One or more of $L^1$, $L^2$ and $L^3$ may comprise a carbene group.

Preferably, compositions described herein comprise a compound of formula (I) and a blue phosphorescent material wherein:

q is 2 or 3 and each $L^1$ is a C,N-bidentate ligand of formula (X);

r is 0 or 1 and $L^2$, if present, is a C,N-bidentate ligand of formula (X) or an O,O—, N,N— or O,N-bidentate ligand;

s is 0;

and M is iridium.

Dendrons as described herein comprise a branching point attached to a ligand of the metal complex and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example $C_{1-20}$ alkyl or alkoxy.

A dendron may have optionally substituted formula (XI)

(XI)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIa):

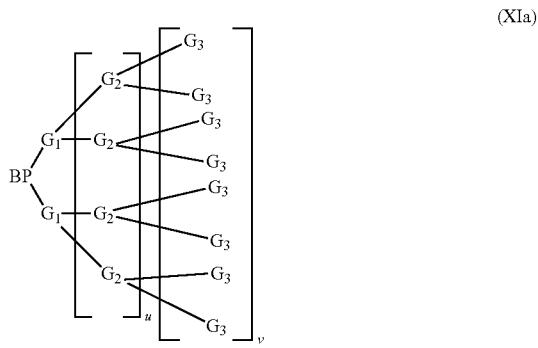

(XIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ ... $G_n$ is phenyl, and each phenyl BP, $G_1$, $G_2$ ... $G_{n-1}$ is a 3,5-linked phenyl.

A preferred dendron is a substituted or unsubstituted dendron of formula (XIb):

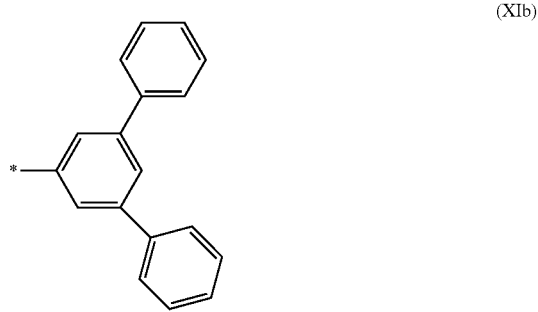 [SMILES: *c1cc(-c2ccccc2)cc(-c2ccccc2)c1]

(XIb)

wherein * represents an attachment point of the dendron to a ligand.

BP and/or any group G may be substituted with one or more substituents, for example one or more $C_{1-20}$ alkyl or alkoxy groups.

Light-emitting material(s) in a composition comprising the compound of formula (I) or (III) and one or more light-emitting materials may make up about 0.05 wt % up to about 50 wt %, optionally about 1-40 wt % of the composition.

Charge Transporting and Charge Blocking Layers

A device containing a light-emitting layer containing a compound of formula (I) or (III) may have charge-transporting and/or charge blocking layers.

A hole transporting layer may be provided between the anode and the light-emitting layer or layers of an OLED. An electron transporting layer may be provided between the cathode and the light-emitting layer or layers.

An electron blocking layer may be provided between the anode and the light-emitting layer(s) and a hole blocking layer may be provided between the cathode and the light-emitting layer(s). Charge-transporting and charge-blocking layers may be used in combination. Depending on the HOMO and LUMO levels of the material or materials in a layer, a single layer may both transport one of holes and electrons and block the other of holes and electrons.

If present, a hole transporting layer located between the anode and the light-emitting layer(s) preferably has a material having a HOMO level of less than or equal to 5.5 eV, more preferably around 4.8-5.5 eV or 4.9-5.3 eV as measured by square wave voltammetry. The HOMO level of the material in the hole transport layer may be selected so as to be within 0.2 eV, optionally within 0.1 eV of the light-emitting material of the light-emitting layer.

A hole-transporting layer may contain polymeric or non-polymeric charge-transporting materials. Exemplary hole-transporting materials contain arylamine groups.

A hole transporting layer may contain a homopolymer or copolymer comprising a repeat unit of formula (VII):

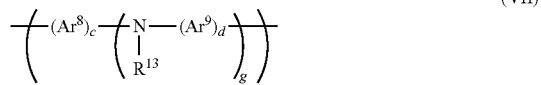
(VII)

wherein $Ar^8$ and $Ar^9$ in each occurrence are independently selected from substituted or unsubstituted aryl or heteroaryl, g is greater than or equal to 1, preferably 1 or 2, $R^{13}$ is H or a substituent, preferably a substituent, and c and d are each independently 1, 2 or 3.

$R^{13}$, which may be the same or different in each occurrence when g>1, is preferably selected from the group consisting of alkyl, for example $C_{1-20}$ alkyl, $Ar^{10}$, a branched or linear chain of $Ar^{10}$ groups, or a crosslinkable unit that is bound directly to the N atom of formula (VIII) or spaced apart therefrom by a spacer group, wherein $Ar^{10}$ in each occurrence is independently optionally substituted aryl or heteroaryl. Exemplary spacer groups are $C_{1-20}$ alkyl, phenyl and phenyl-$C_{1-20}$ alkyl.

Any of $Ar^8$, $Ar^9$ and, if present, $Ar^{10}$ in the repeat unit of Formula (VII) may be linked by a direct bond or a divalent linking atom or group to another of $Ar^8$, $Ar^9$ and $Ar^{10}$. Preferred divalent linking atoms and groups include O, S; substituted N; and substituted C.

Any of $Ar^8$, $Ar^9$ and, if present, $Ar^{10}$ may be substituted with one or more substituents. Exemplary substituents are substituents $R^{10}$, wherein each $R^{10}$ may independently be selected from the group consisting of:

substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F; and a crosslinkable group attached directly to $Ar^8$, $Ar^9$ or $Ar^{10}$ or spaced apart therefrom by a spacer group, for example a group comprising a double bond such and a vinyl or acrylate group, or a benzocyclobutane group Preferred repeat units of formula (VII) have formulae 1-3:

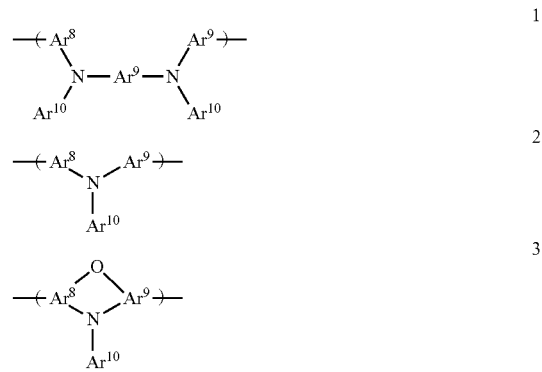

In one preferred arrangement, $R^{13}$ is $Ar^m$ and each of $Ar^8$, $Ar^9$ and $Ar^m$ are independently and optionally substituted with one or more $C_{1-20}$ alkyl groups. $Ar^8$, $Ar^9$ and $Ar^{10}$ are preferably phenyl.

In another preferred arrangement, the central $Ar^9$ group of formula (1) linked to two N atoms is a polycyclic aromatic that may be unsubstituted or substituted with one or more substituents $R^{10}$. Exemplary polycyclic aromatic groups are naphthalene, perylene, anthracene and fluorene.

In another preferred arrangement, $Ar^8$ and $Ar^9$ are phenyl, each of which may be substituted with one or more $C_{1-20}$ alkyl groups, and $R^{13}$ is —$(Ar^{10})_r$, wherein r is at least 2 and wherein the group —$(Ar^{10})_r$, forms a linear or branched chain of aromatic or heteroaromatic groups, for example 3,5-diphenylbenzene wherein each phenyl may be substituted with one or more $C_{1-20}$ alkyl groups. In another preferred arrangement, c, d and g are each 1 and $Ar^8$ and $Ar^9$ are phenyl linked by an oxygen atom to form a phenoxazine ring.

A hole-transporting polymer containing repeat units of formula (VII) may be a copolymer containing one or more further repeat units. Exemplary further repeat units include arylene repeat units, each of which may be unsubstituted or substituted with one or more substituents.

Exemplary arylene repeat units include without limitation, fluorene, phenylene, naphthalene, anthracene, indenofluorene, phenanthrene and dihydrophenanthrene repeat units, each of which may be unsubstituted or substituted with one or more substituents.

Substituents of arylene repeat units, if present, may be selected from $C_{1-40}$ hydrocarbyl, preferably $C_{1-20}$ alkyl; phenyl which may be unsubstituted or substituted with one or more $C_{1-10}$ alkyl groups; and crosslinkable hydrocarbyl groups, for example $C_{1-40}$ hydrocarbyl groups comprising benzocyclobutene or vinylene groups.

Phenylene repeat units may be 1,4-linked phenylene repeat units that may be unsubstituted or substituted with 1, 2, 3 or 4 substituents. Fluorene repeat units may be 2,7-linked fluorene repeat units.

Fluorene repeat units preferably have two substituents in the 9-position thereof. Aromatic carbon atoms of fluorene repeat units may each independently be unsubstituted or substituted with a substituent.

If present, an electron transporting layer located between the light-emitting layers and cathode preferably has a LUMO level of around 1.8-2.7 eV as measured by square wave voltammetry. An electron-transporting layer may have a thickness in the range of about 5-50 nm.

A charge-transporting layer or charge-blocking layer may be crosslinked, particularly if a layer overlying that charge-transporting or charge-blocking layer is deposited from a solution. The crosslinkable group used for this crosslinking may be a crosslinkable group comprising a reactive double bond such and a vinyl or acrylate group, or a benzocyclobutane group. The crosslinkable group may be provided as a substituent of, or may be mixed with, a charge-transporting or charge-blocking material used to form the charge-transporting or charge-blocking layer.

A charge-transporting layer adjacent to a light-emitting layer containing a phosphorescent light-emitting material preferably contains a charge-transporting material having a lowest triplet excited state ($T_1$) excited state that is no more than 0.1 eV lower than, preferably the same as or higher than, the $T_1$ excited state energy level of the phosphorescent light-emitting material(s) in order to avoid quenching of triplet excitons.

A charge-transporting layer as described herein may be non-emissive, or may contain a light-emitting material such that the layer is a charge transporting light-emitting layer. If the charge-transporting layer is a polymer then a light-emitting dopant may be provided as a side-group of the polymer, a repeat unit in a backbone of the polymer, or an end group of the polymer. Optionally, a hole-transporting polymer as described herein comprises a phosphorescent polymer in a side-group of the polymer, in a repeat unit in a backbone of the polymer, or as an end group of the polymer.

The polystyrene-equivalent number-average molecular weight (Mn) measured by gel permeation chromatography of the polymers described herein may be in the range of about $1 \times 10^3$ to $1 \times 10^8$, and preferably $1 \times 10^4$ to $5 \times 10^6$. The polystyrene-equivalent weight-average molecular weight (Mw) of the polymers described herein may be $1 \times 10^3$ to $1 \times 10^8$, and preferably $1 \times 10^4$ to $1 \times 10^7$.

Polymers as described herein are suitably amorphous.

Hole Injection Layers

A conductive hole injection layer, which may be formed from a conductive organic or inorganic material, may be provided between the anode 101 and the light-emitting layer 103 of an OLED as illustrated in FIG. 1 to assist hole injection from the anode into the layer or layers of semi-conducting polymer. Examples of doped organic hole injection materials include optionally substituted, doped poly(ethylene dioxythiophene) (PEDOT), in particular PEDOT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx, MoOx and RuOx as disclosed in Journal of Physics D: Applied Physics (1996), 29(11), 2750-2753.

Cathode

The cathode 105 is selected from materials that have a work function allowing injection of electrons into the light-emitting layer of the OLED. Other factors influence the selection of the cathode such as the possibility of adverse interactions between the cathode and the light-emitting material. The cathode may consist of a single material such as a layer of aluminium. Alternatively, it may comprise a plurality of conductive materials such as metals, for example a bilayer of a low work function material and a high work function material such as calcium and aluminium, for example as disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a work function of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a charge-transporting or light-emitting layer may be formed from a compound of formula (I) or (III), any further components of the layer such as light-emitting dopants, and one or more suitable solvents.

The formulation may be a solution of the compound of formula (I) or (III) and any other components in the one or more solvents, or may be a dispersion in the one or more solvents in which one or more components are not dissolved. Preferably, the formulation is a solution.

Solvents suitable for dissolving compounds of formula (I) or (III) are benzenes substituted with one or more $C_{1-10}$ alkyl or $C_{1-10}$ alkoxy groups, for example toluene, xylenes and methylanisoles.

Particularly preferred solution deposition techniques including printing and coating techniques such spin-coating, inkjet printing and slot-die coating.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Compound Example 1

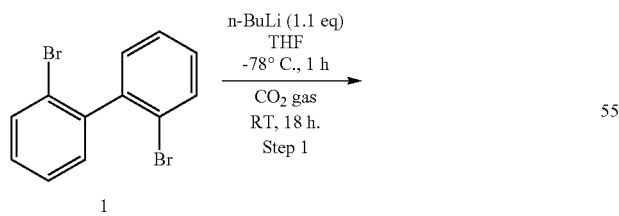

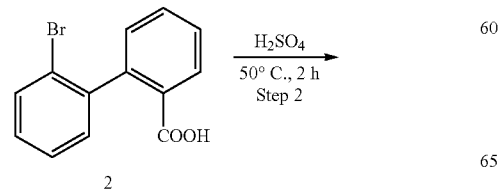

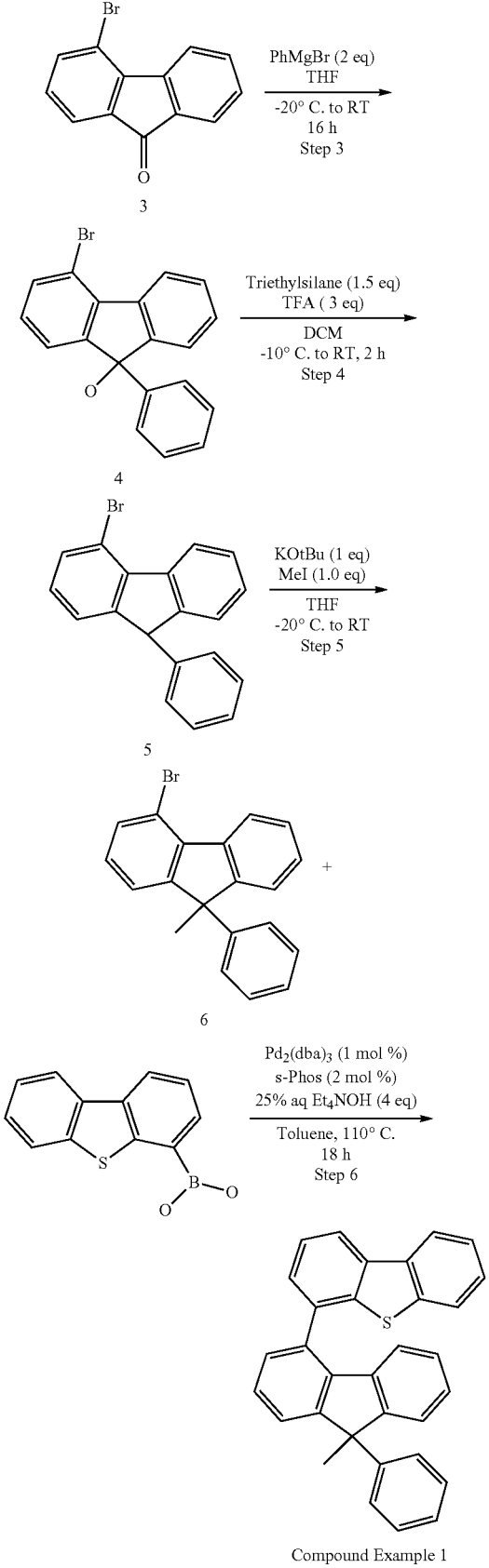

Compound Example 1

Step 1:

Apparatus Set-Up:

A 5 L 3-necked round-bottomed flask, equipped with a mechanical overhead stirrer, nitrogen inlet and exhaust.

Experimental Procedure 2,2'-dibromo biphenyl (100 g, 0.3205 mol) was taken in dry deoxygenated tetrahydrofuran (1400 mL). The reaction mixture was cooled to −78° C. using dry ice/acetone bath. 2.5M n-BuLi in hexane (144 mL, 0.3525 mol) was slowly added. The reaction mixture was stirred at −78° C. for an hour. After 1 h, $CO_2$ gas was purged at −78° C. for 2 h. The reaction mixture was slowly allowed to room temperature and stirred for 18 h. The reaction mixture was quenched with water (500 mL) and extracted with diethylether (3×500 mL). The combined organic phase was washed with water (300 mL), brine (300 mL), dried over sodium sulphate and concentrated to get 70 g of intermediate 2. The crude product was used as such in the next step without purification.

Step 2

Apparatus Set-Up:

A 2 L 3-necked round-bottomed flask, equipped with a mechanical overhead stirrer, nitrogen inlet and exhaust.

Experimental Procedure

To the crude intermediate 2 (70 g, 0.2525 mol), conc. $H_0SO_4$ (1400 mL) was slowly added at 0° C. The reaction mixture was heated to 50° C. and stirred for 2 h. After 2 h, LCMS monitoring showed complete conversion of starting material. After cooling to room temperature, the mixture was carefully poured into ice water (1000 mL) and stirred for an hour. The precipitated solid was filtered and washed with water (500 mL). The crude product was purified twice by hot acetone crystallization to get 36 g intermediate 3 with 99.54% HPLC purity.

Step 3

Apparatus Set-Up:

A 1 L 3-necked round-bottomed flask, equipped with a magnetic stirrer, nitrogen inlet and exhaust.

Experimental Procedure

Intermediate 3 (55 g, 0.2122 mol) was dissolved in dry deoxygenated tetrahydrofuran (600 mL). The solution was cooled to −20° C. 1 M Phenyl magnesium bromide in THF (424.5 mL, 0.4245 mol) was slowly added. The reaction mixture was stirred at room temperature for 18 h. After 18 h, crude LCMS analysis showed complete conversion of starting material. The reaction mixture was quenched with water (300 mL) and extracted with EtOAc (3×500 mL). The combined organic phase was washed with water (300 mL), brine (300 mL), dried over sodium sulphate and concentrated. The crude intermediate 4 (66 g) was taken to next step without purification.

Step 4

Apparatus Set-Up:

A 1 L 3-necked round-bottomed flask, equipped with a magnetic stirrer, nitrogen inlet and exhaust.

Experimental Procedure

Intermediate 4 (66 g, 0.1957 mol) and Triethyl silane (34.13 g, 0.2935 mol) were taken in dry deoxygenated dichloromethane (700 mL). The reaction mixture was cooled to −10° C. Trifluoro aceticacid (66.94 g, 0.5871 mol) was slowly added. The reaction mixture was stirred at room temperature for 2 h. Crude GCMS analysis showed complete conversion of starting material. The reaction mixture was quenched with water (300 mL) and extracted with ethyl acetate (3×500 mL). The combined organic phase was washed with water (300 mL), brine (300 mL), dried over sodium sulphate and concentrated. The crude residue (70 g) was purified by silica column chromatography using 1% ethyl acetate in hexane as an eluent to get 52 g of intermediate 5 with 97.65% HPLC purity.

Step 5

Apparatus Set-Up:

A 1 L 3-necked round-bottomed flask, equipped with a magnetic stirrer, nitrogen inlet and exhaust.

Experimental Procedure

To deoxygenated dry THF (300 mL), potassium tert-butoxide (18.16 g, 0.1618 mol) was added and the solution purged with nitrogen for one hour. Intermediate 5 (52 g, 0.1618 mol) was dissolved in dry tetrahydrofuran (300 mL) and purged with nitrogen for one hour. The reaction mixture was cooled to −20° C. Methyl iodide (22.97 g, 0.1618 mol) and potassium tert-butoxide solution (degassed) were added drop wise to the reaction mixture. The reaction mixture was slowly allowed to room temperature and stirred for 16 h. The reaction mixture was quenched with water (300 mL) and extracted with ethyl acetate (3×500 mL). The combined organic phase was washed with water (300 mL), brine (300 mL), dried over sodium sulphate and concentrated (60 g). The crude product (60 g) was purified by silica column chromatography using 5% ethyl acetate in hexane as an eluent. The pure fractions obtained were (52 g) recrystallised twice from hot acetonitrile (6 vol) to obtain 42 g of intermediate 6 with 99.12% HPLC purity.

Step 6

Apparatus Set-Up:

A 500 mL 3-necked round-bottomed flask, equipped with a magnetic stirrer, reflux condenser, nitrogen inlet and exhaust.

Experimental Procedure

A mixture of intermediate 6 (15 g, 0.0447 mol) and dibenzothiophene-4-boronic acid (15.3 g, 0.0671 mol) in toluene (200 mL), was purged with nitrogen for an hour. In another container, aqueous 25% Tetraethyl ammonium hydroxide (105.3 mL and 0.1789 mol) solution was purged with nitrogen for an hour. The reaction mixture was heated to 60° C. S-phos (0.36 g, 0.00089 mol) and $Pd_2(dba)_3$ (0.41 g, 0.00044 mol) were added at 60° C. The degassed tetraethyl ammonium hydroxide was added and refluxed at 110° C. for 18 h. The reaction mixture filtered and washed with toluene. The organic phase was washed with water (400 mL), brine (300 mL), dried over sodium sulphate and the solvent removed. The crude product was purified by silica column chromatography using 5% ethyl acetate in hexane as an eluent to get 22 g. The 22 g fraction was recrystallized twice from hot acetonitrile to get 16.8 g with 99.90% purity. The compound was dissolved in dichloromethane, heated to 45° C., filtered whilst hot and the solvent removed to obtain 16.66 g of compound example 1 with 99.90% HPLC purity.

1H-NMR (400 MHz, CDCl3): δ 1.98-2.00 (m, 3H), 6.50-6.55 (m, 1H), 6.86-6.88 (m, 1H), 7.10-7.11 (m, 1H), 7.19-7.23 (m, 1H), 0.24-7.28 (m, 2H), 7.29-7.36 (m, 4H), 7.37-7.38 (m, 3H), 7.45-7.49 (m, 2H), 7.49-7.51 (m, 1H), 7.59-7.61 (m, 1H), 7.67-7.77 (m, 1H), 8.27-8.32 (m, 1H).

Compound example 1 was then sublimed at a pressure of $1 \times 10^{-7}$ mbar at a temperature of 200° C. prior to use for testing.

Compound Example 2

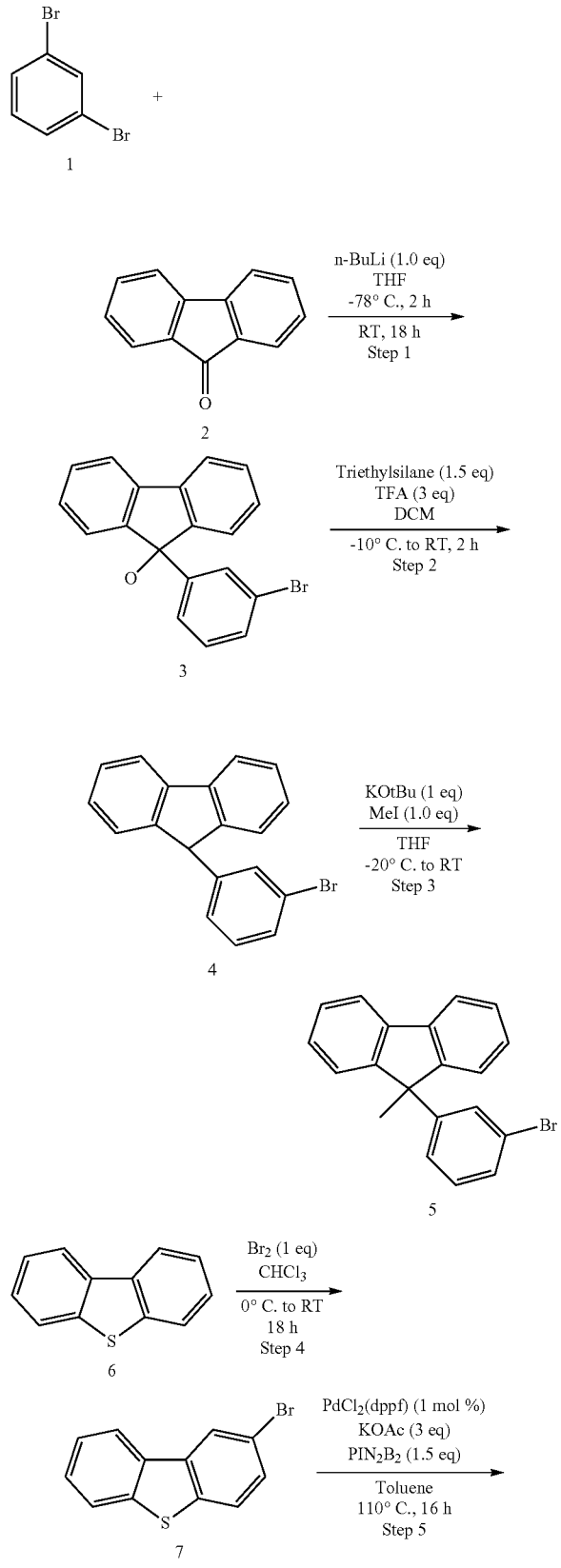

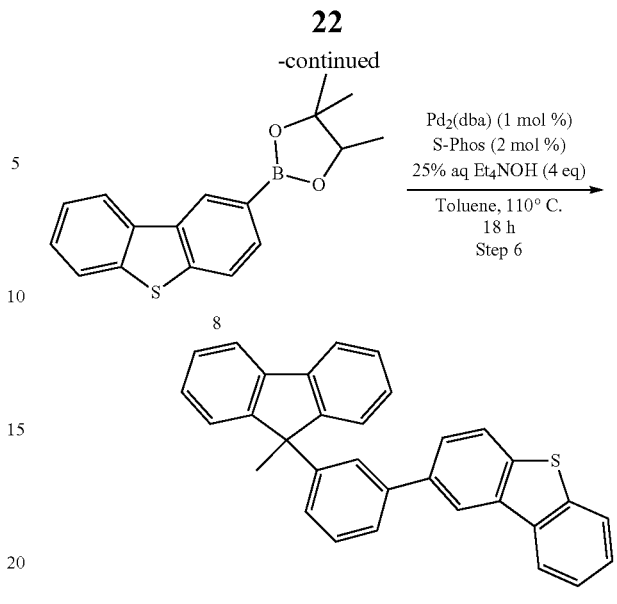

Compound example 2

Step 1

Apparatus Set-Up:

A 10 L 3-necked round-bottomed flask, equipped with a mechanical overhead stirrer, nitrogen inlet and exhaust.

Experimental Procedure 1,3-dibromobenzene (288 g, 1.220 mol) was taken in dry deoxygenated tetrahydrofuran (2 L) and cooled to −78° C. 2.5M n-butyl lithium in hexane (443 mL, 1.109 mol) was slowly added and stirred at the same temperature for 2 h. 9-Fluorenone (200 g, 1.109 mol) in THF (500 mL) was slowly added at the same temperature. The reaction mixture was allowed to room temperature and stirred for 18 h. The reaction was quenched with saturated $NH_4Cl$ solution (200 mL) and extracted with EtOAc (3×1 L). The combined organic phase was washed with water (1000 mL), brine (500 mL), dried over sodium sulphate and concentrated. The solid obtained contained ~60% desired product. The crude mixture was used in the next step without further purification.

Step 2

Apparatus Set-Up:

A 10 L 3-necked round-bottomed flask, equipped with a mechanical overhead stirrer, nitrogen inlet and exhaust.

Experimental Procedure

Intermediate 1 (~60% pure, 420 g, 0.771 mol) and Triethyl silane (186 mL, 1.156 mol) were taken in dry deoxygenated dichloromethane (3 L). The reaction mixture was cooled to −10° C. and stirred for 0.5 h. Trifluoroacetic acid (175 mL, 2.313 mol) was slowly added. The reaction mixture was stirred at room temperature for 2 h. GCMS analysis showed complete conversion of starting material. The reaction mixture was quenched with water (300 mL). The organic phase was washed with water (500 mL), brine (500 mL), dried over sodium sulphate and concentrated to obtain 326 g of crude product. The crude residue was purified by silica column chromatography using 3 to 4% ethyl acetate in hexane as an eluent and the product was triturated with methanol to obtain 216 g of intermediate 2 with 92.9% HPLC purity. It was further recrystallized from hot acetonitrile to get 195 g of intermediate 4 with 97.02% purity by HPLC.

Step 3
Apparatus Set-Up:
A 10 L 3-necked round-bottomed flask, equipped with a mechanical overhead stirrer, nitrogen inlet and exhaust.
Experimental Procedure In the reaction flask Intermediate 2 (195 g, 0.607 mol) was dissolved in dry tetrahydrofuran (1800 mL) and purged with nitrogen for an hour, and then cooled to −20° C. In a separate flask to dry deoxygenated THF (1200 mL), Potassium tert-butoxide (68.1 g, 0.607 mol) was added and purged with nitrogen for an hour. Methyl iodide (37.9 mL, 0.607 mol) and potassium tert-butoxide solution were added drop wise to the reaction mixture. The reaction mixture was slowly allowed to room temperature and stirred for 18 h. The reaction mixture was quenched with NH$_4$Cl solution (500 mL) and extracted with ethyl acetate (3×1 L). The combined organic phase was washed with water (1 L), brine (500 mL), dried over sodium sulphate and the solvent removed. The crude product (210 g) was purified by silica column chromatography using 5 to 6% ethyl acetate in hexane as an eluent. The pure fractions obtained were purified by recrystallising twice from hot methanol to get 155 g of Intermediate 3 with 99.19% HPLC purity.

Step 4
Apparatus Set-Up:
A 1 L 4-necked round-bottomed flask, equipped with an overhead stirrer, nitrogen inlet and exhaust.
Experimental Procedure To a solution of dibenzothiophene (4) (15 g, 0.0811 mol) in chloroform (90 mL), Bromine (4.17 mL, 0.0811 mol) in DCM (30 mL) was slowly added at 0° C. The reaction mixture was stirred at RT for 18 h. Analysis of the reaction mixture by GCMS showed 5% of dibromide and 10% of dibenzothiophene. The reaction mixture was quenched with water and the organic layer washed with sodium thiosulphate and concentrated to get 19 g of yellow solid. It was taken in toluene (100 mL), heated to 80° C. and cooled to RT and the solid was filtered to get 9 g of intermediate 5 with 93.43% HPLC purity.

Step 5
Apparatus Set-Up:
A 1 L 3-necked round-bottomed flask, equipped with a mechanical overhead stirrer, condenser, nitrogen inlet and exhaust.
Experimental Procedure Intermediate 5 (9 g, 0.0341 mol), bis(pinacolato)diborane (13 g, 0.0512 mol), potassium acetate (10.04 g, 0.102 mol) were taken in toluene (100 mL). The reaction mixture was degassed with N$_2$ gas for 30 minutes. PdCl$_2$(dppf) (0.27 g, 0.0003 mol) was added. The reaction mixture was heated to 110° C. for 16 h. After complete conversion, the reaction mixture was cooled to room temperature and filtered through a celite bed. The solvent was removed under vacuum to obtain the crude product (19 g) The crude product was triturated with hexane and filtered to get 16.6 g with 91.67% HPLC purity. It was used as such in next step.

Step 6
Apparatus Set-Up:
A 1 L 3-necked round-bottomed flask, equipped with a mechanical overhead stirrer, reflux condenser, nitrogen inlet and exhaust.
Experimental Procedure To a mixture of 3 (12 g, 0.035 mol) and intermediate 6 (16.6 g, 0.053 mol) in toluene (240 mL), N$_2$ gas was purged for an hour. In another container, aqueous 25% Tetraethyl ammonium hydroxide (82.4 mL, 0.14 mol) solution was degassed with N$_2$ for 1 h. The reaction mixture was heated to 60° C. S-phos (0.28 g, 0.0007 mol) and Pd$_2$(dba)$_3$ (0.32 g, 0.0003 mol) were added at 60° C. The degassed tetraethyl ammonium hydroxide was added and refluxed at 110° C. for 18 h. The reaction mixture filtered and washed with toluene. The organic phase was washed with water (400 mL), brine (300 mL), dried over sodium sulphate and concentrated (18 g). The crude product was purified by silica column chromatography using 5% ethyl acetate in hexane as an eluent to get 14 g with 84.6% HPLC purity. It was recrystallized twice with hot toluene/acetonitrile to get 8 g of Compound example 2 with 99.69% purity.

1H-NMR (400 MHz, CDCl3): δ 1.98 (s, 3H), 6.50-6.55 (m, 1H), 6.86-6.88 (m, 1H), 7.10-7.11 (m, 1H), 7.19-7.23 (m, 1H), 0.24-7.28 (m, 2H), 7.29-7.36 (m, 4H), 7.37-7.38 (m, 3H), 7.45-7.49 (m, 2H), 7.49-7.51 (m, 1H), 7.59-7.61 (m, 1H), 7.67-7.77 (m, 1H), 8.27-8.32 (m, 1H).

Compound example 2 was sublimed prior to testing at $10^{-7}$ mbar, 225° C.

HOMO and LUMO levels of Compound Examples 1-4 and of Comparative Example 1 are given in Table 1.

TABLE 1

| Compound | HOMO (eV) | LUMO (eV) |
|---|---|---|
| Comparative Compound 1 | −5.69 | −1.96 |
| Compound Example 1 | −6.02 | −1.92 |
| Compound Example 2 | −5.92 | −1.84 |

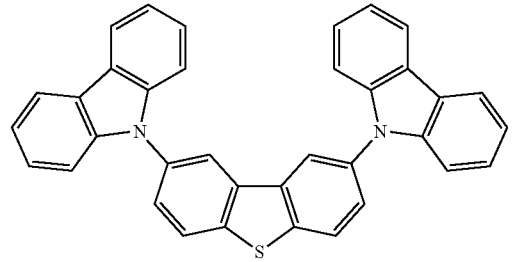

Comparative Compound 1

As shown in Table 1, the HOMO levels of the exemplary compounds are significantly deeper than that of the comparative compound. The LUMO levels are similar.

HOMO and LUMO values were measured by square wave voltammetry.

Apparatus for HOMO or LUMO energy level measurements by SWV comprise a CHI 660D Potentiostat; a 3 mm diameter glassy carbon working electrode; a leak free Ag/AgCl reference electrode; Pt wire counter electrode; and a cell containing 0.1M tetrabutylammonium hexafluorophosphate in acetonitrile:toluene (1:1).

A cell containing 0.1M tetrabutylammonium hexafluorophosphate in acetonitrile:toluene (1:1) was used and Ferrocene is added to a fresh cell of identical solvent composition for calculation purposes where the potentials are determined for the oxidation and reduction of ferrocene versus Ag/AgCl using cyclic voltammetry (CV). The sample was dissolved in Toluene (3 mg/ml) and added directly to the cell LUMO=4.8-E ferrocene(peak to peak average)−E reduction of sample(peak maximum)

HOMO=4.8-E ferrocene(peak to peak average)+E oxidation of sample(peak maximum)

The SWV experiment was run at 15 Hz frequency; 25 mV amplitude and 0.004V increment steps under an Argon gas purge.

COMPOSITION EXAMPLES

The stabilities of compositions of host compounds (75 wt %) and Green Phosphorescent Emitter 1 (25 wt %) were measured by irradiating the compositions with ultraviolet light and measuring the time taken for luminance of the composition to fall to 80% of an initial value ($T_{80}$).

Films of 80 nm thickness were spun on glass substrates and encapsulated, with the inclusion of a getter. The films were irradiated using a laser diode of wavelength 405 nm, focused to a spot size of 1 mm². The total PL counts were integrated over the range 450-650 nm using a confocal geometry and an ocean optics USB200 spectrometer. The time taken for the total PL counts to fall to 80% of the initial value ($T_{80}$) was recorded.

The intensity of irradiation was adjusted so that the luminance of the film comprising Comparative Compound 1 reached $T_{80}$ over a timescale of 1 to 2 hours.

The film comprising Compound Example 1 was then irradiated in the same manner, with the intensity of the 405 nm radiation adjusted so as to give the same initial number of PL counts as that of the film comprising Comparative Compound 1.

The results as set out in Table 2 show much greater stability for the inventive hosts than Comparative Compound 1.

TABLE 2

| Host | $T_{80}$ (relative to Comparative Compound 1) |
|---|---|
| Comparative Compound 1 | 1.0 |
| Compound Example 1 | 4.0 |

Green Phosphorescent Emitter 1

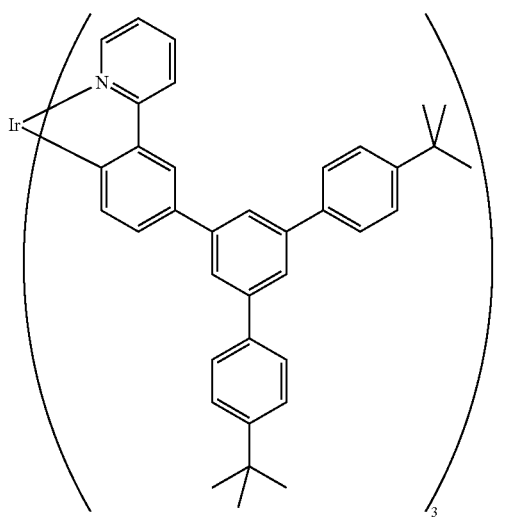

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A compound of formula (I)

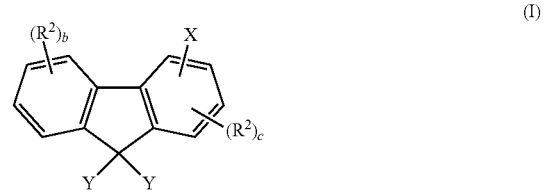

wherein:
one Y is a substituent $R^1$ bound directly to the fluorene unit of formula (I) by an sp³-hybridised carbon atom, wherein $R^1$ is a $C_{1-20}$ alkyl group;
the other Y is a phenyl that may be unsubstituted or substituted with one or more substituents;
$R^2$ is a linear, branched or cyclic $C_{1-12}$ alkyl; or aryl or heteroaryl which is unsubstituted or substituted with one or more $C_{1-12}$ alkyl groups;
b is 0, 1, 2, 3 or 4;
c is 0, 1, 2 or 3; and
X is a group of formula (II):

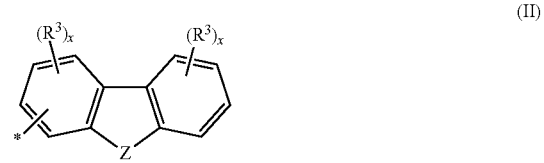

wherein Z is O or S; $R^3$ independently in each occurrence is a substituent; each x is independently 0, 1, 2 or 3; and * is a bond to the fluorene unit of formula (I).

2. A compound according to claim 1 wherein the group of formula (II) has formula (IIa):

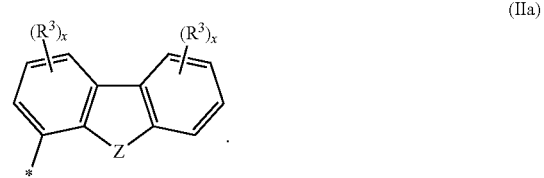

3. A compound according to claim 1 wherein the group of formula (II) has formula (IIb):

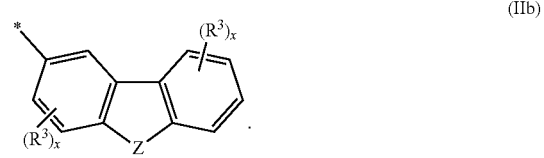

4. A composition comprising a compound according to claim 1 and at least one light-emitting dopant.

5. A composition according to claim 4 wherein the light-emitting dopant is a phosphorescent dopant.

6. A composition according to claim 5 wherein the light-emitting dopant is a blue light-emitting material.

7. A composition according to claim 6 wherein the light-emitting dopant is a metal complex comprising at least one unsubstituted or substituted phenylimidazole or phenyltriazole ligand.

8. A formulation comprising a compound according to claim 1 and one or more solvents.

9. An organic light-emitting device comprising an anode, a cathode and a light-emitting layer between the anode and the cathode wherein the light-emitting layer comprises a compound according to claim 1.

10. An organic light-emitting device according to claim 9 wherein the organic light-emitting layer comprises a composition comprising the compound and at least one light-emitting dopant.

11. An organic light-emitting device comprising an anode, a cathode, a light-emitting layer between the anode and the cathode, and at least one further light-emitting layer, wherein the light-emitting layer comprises a compound of formula (I):

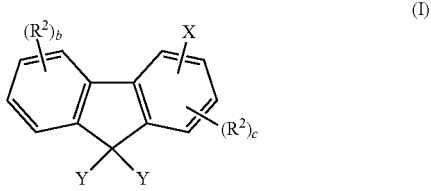

(I)

wherein:
one Y is a substituent $R^1$ bound directly to the fluorene unit of formula (I) by an $sp^3$-hybridised carbon atom;
the other Y is a phenyl that may be unsubstituted or substituted with one or more substituents;
$R^2$ is a linear, branched or cyclic $C_{1-12}$ alkyl; or aryl or heteroaryl which is unsubstituted or substituted with one or more $C_{1-12}$ alkyl groups;
b is 0, 1, 2, 3 or 4;
c is 0, 1, 2 or 3; and
X is a group of formula (II):

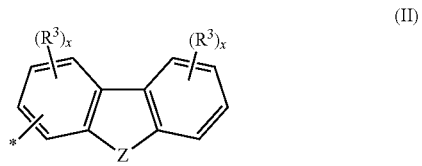

(II)

wherein Z is O or S; $R^3$ independently in each occurrence is a substituent; each x is independently 0, 1, 2 or 3; and * is a bond to the fluorene unit of formula (I).

12. An organic light-emitting device comprising an anode, a cathode and a light-emitting layer between the anode and the cathode, wherein the device emits white light, and wherein the light-emitting layer comprises a compound of formula (I):

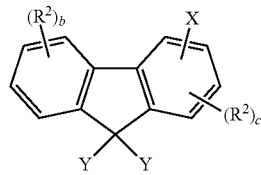

(I)

wherein:
one Y is a substituent $R^1$ bound directly to the fluorene unit of formula (I) by an $sp^3$-hybridised carbon atom;
the other Y is a phenyl that may be unsubstituted or substituted with one or more substituents;
$R^2$ is a linear, branched or cyclic $C_{1-12}$ alkyl; or aryl or heteroaryl which is unsubstituted or substituted with one or more $C_{1-12}$ alkyl groups;
b is 0, 1, 2, 3 or 4;
c is 0, 1, 2 or 3; and
X is a group of formula (II):

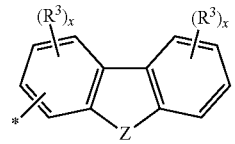

(II)

wherein Z is O or S; $R^3$ independently in each occurrence is a substituent; each x is independently 0, 1, 2 or 3; and * is a bond to the fluorene unit of formula (I).

13. A method of forming an organic light-emitting device according to claim 9 comprising the step of forming the light-emitting layer over one of the anode and the cathode and forming the other of the anode and the cathode over the light-emitting layer.

14. A method according to claim 13 wherein the light-emitting layer is formed by depositing a formulation comprising the compound and one or more solvents and evaporating the one or more solvents.

15. An organic light-emitting device comprising an anode, a cathode and a light-emitting layer between the anode and the cathode wherein the light-emitting layer comprises a composition comprising at least one light-emitting dopant and a compound of formula (I)
wherein:

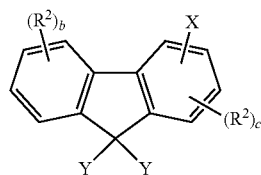

(I)

one Y is a substituent $R^1$ bound directly to the fluorene unit of formula (I) by an $sp^3$-hybridised carbon atom;
the other Y is an aryl or heteroaryl group $Ar^1$ that may be unsubstituted or substituted with one or more substituents;
$R^2$ is a substituent;
b is 0, 1, 2, 3 or 4;
c is 0, 1, 2 or 3; and X is a group of formula (II):

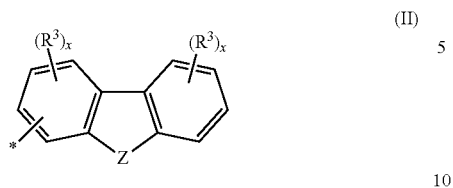

wherein Z is O or S; $R^3$ independently in each occurrence is a substituent; each x is independently 0, 1, 2 or 3; and * is a bond to the fluorene unit of formula (I);

wherein the device comprises at least one further light-emitting layer.

16. The compound according to claim 1 wherein b and c are each 0.

17. The organic light-emitting device according to claim 11 wherein b and c are each 0.

18. The organic light-emitting device according to claim 12 wherein b and c are each 0.

* * * * *